Dec. 6, 1960 E. S. BOERNER Plant Pat. 1,996
CHRYSANTHEMUM PLANT
Filed Feb. 26, 1960
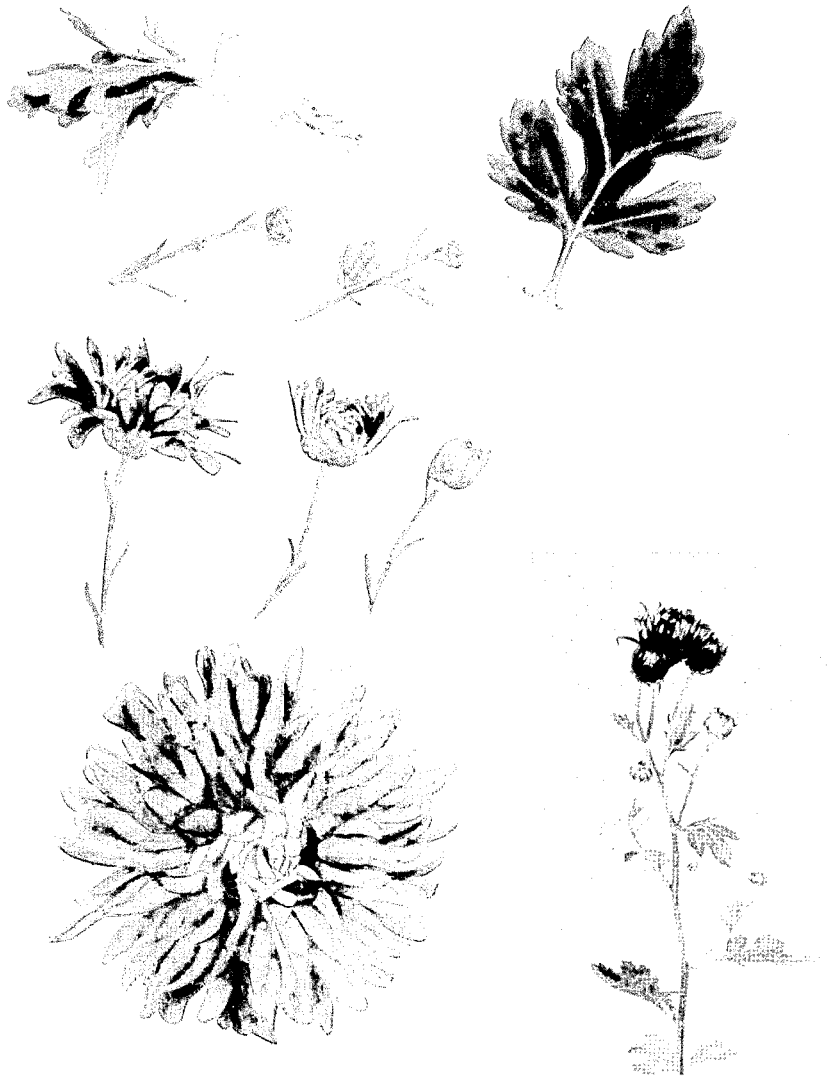
Inventor.
E. S. Boerner
By: Robb & Robb
Attorneys.

United States Patent Office

Plant Pat. 1,996
Patented Dec. 6, 1960

1,996

CHRYSANTHEMUM PLANT

Eugene S. Boerner, Newark, N.Y., assignor to Jackson & Perkins Company, Newark, N.Y., a corporation of New York Filed Feb. 26, 1960, Ser. No. 11,394

1 Claim. (Cl. 47—60)

The present invention relates to a new and distinct variety of chrysanthemum plant of the decorative class, which was discovered by me as a sport of the variety known as "Kingfisher" (Plant Patent No. 1548).

At the time of my initial discovery of the new sport referred to above, plants of the patented variety "Kingfisher" were being grown under my direction and supervision in the fields of my assignee, said fields being located at Newark, New York. During the course of these growing operations, my attention was attracted to one plant which appeared to be bearing flowers differing in color from the normal color of the flowers of the variety "Kingfisher." Upon closer observation of this plant, I found that it had sported, and I thereupon immediately took steps to carefully preserve the sport and keep it under observation. In addition, I also took steps to asexually reproduce the sport by both top cuttings and underground runners, as performed in the fields aforementioned at Newark, New York. Continued observations of the original sport and the asexual reproductions thereof conclusively showed that the new flower color of the sport was fully established and fixed, and comes true to form by asexual propagation.

Other improved features were also found in the new sport in the course of prolonged observations thereof, these features, together with the new flower color, constituting a desirable and unique combination which definitely differentiates the sport from its parent, as well as from all other chrysanthemum varieties of which I am aware. The most outstanding and significant features of this new combination are as follows:

(1) A general similarity in habit of growth and form to those of the parent variety "Kingfisher";

(2) Glossy dark green foliage;

(3) A distinctive flower color which may be briefly described as "Carmine," lightly overcast with Spectrum Red; and (4) Freedom of reproduction by suckers, which is unusual in chrysanthemum varieties which bear flowers in the red color range.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen plant which is depicted in black-and-white for the purpose of illustrating the form and habit of growth of the plant.

The following is a detailed description of the new variety, with color terminology in accordance with Ridgway's Color Standards and Nomenclature, as based upon observations made from specimens grown outdoors at Newark, New York, near mid-morning during the early part of the month of October:

Parentage: Sport of "Kingfisher."
Classification: Decorative.
Growth: Medium tall.
Cold resistance: Plants are very winter hardy in northern New York, and flowers are frost resistant.
Blooming period: In the Newark, New York, climatic area, the average date of start of bloom is about October 15th, with blooms continuing until heavy frost.

*Flower*

Bud:
- *Color.*—When sepals first divide—Eugenia Red, Plate 13, with lower half of petals lightly overcast with Pale Yellow-Orange, Plate 3. When petals begin to unfurl—Nopal Red, Plate 1. When half-blown: inside of petals—Carmine, Plate 1, lightly overcast with Spectrum Red, Plate 1; outside of petals—Antimony Yellow, Plate 15, lightly overcast with carmine, Plate 1.
- *Peduncle.*—Color—Light Cress Green, Plate 31. Strength—strong.

Bloom:
- *Size.*—4½".
- *Stem.*—Short; strong.
- *Form.*—Decorative.
- *Petalage.*—Double; wide.
- *Color.*—Center of flower—Ochraceous-Buff, Plate 15, lightly overcast with Spectrum Red, Plate 1. Outer petals—Scarlet-Red, Plate 1, lightly overcast with Nopal Red, Plate 1. Base of petals—Citron Yellow, Plate 16. Inside of Petals—Carmine, Plate 1, lightly overcast with Spectrum Red, Plate 1. Reverse of Petals—Antimony Yellow, Plate 15, light overcast with Nopal Red, Plate 1.
- *Petals.*—Texture—Medium. Form—oval.
- *Fragrance.*—Characteristic chrysanthemum.

*Plant*

Form: Upright; compact.
Growth: Free; many suckers.
Foliage:
- *Size.*—Medium.
- *Quantity.*—Heavy.
- *Color.*—Upper side—Varley's Green, Plate 18. Under side—Cress Green, Plate 31.
- *Texture.*—Leathery; glossy.

I claim:

A new and distinct variety of chrysanthemum plant of the decorative class, substantially as herein shown and described, characterized particularly as to novelty by the unique combination of a general similarity to the variety "Kingfisher" (Plant Patent No. 1,548), glossy, dark green foliage, a distinctive flower color corresponding to Carmine, lightly overcast with Spectrum Red, and an unusual freedom of reproduction by suckers.

No references cited.